(12) United States Patent
Mehul et al.

(10) Patent No.: US 6,800,609 B1
(45) Date of Patent: Oct. 5, 2004

(54) ISOLATED PEPTIDE OF THE HORNY LAYER AND USER THEREOF

(75) Inventors: Bruno Mehul, Villejuif (FR); Dominique Bernard, Paris (FR); Lucie Simonetti, Vincennes (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/031,403

(22) PCT Filed: Apr. 20, 2000

(86) PCT No.: PCT/FR00/01048

§ 371 (c)(1),
(2), (4) Date: Jul. 24, 2002

(87) PCT Pub. No.: WO01/07604

PCT Pub. Date: Feb. 1, 2001

(51) Int. Cl.[7] .................. A61K 38/16; C07K 14/435
(52) U.S. Cl. ............... 514/12; 530/350; 514/863; 514/78.02; 536/523.5; 424/134.1
(58) Field of Search .................. 530/350; 514/12, 514/863, 78.02; 424/134.1; 536/523.5; 435/69.1, 320.1

(56) References Cited

U.S. PATENT DOCUMENTS 6,046,315 A * 4/2000 Hillman et al. ............ 536/23.5

FOREIGN PATENT DOCUMENTS

FR 2 761 363 10/1998

OTHER PUBLICATIONS

Database EMBL/HINXTON, U.K. "Online" "nI01f09,y5 NCL_CGAP_8r2 Homo sapiens cDNA clone IMAGE:966761 5' similar to SW: CALM_PLAFA P24044 CALMODULIN" XP002137649.

B. Mehul, et al., "Identification and Cloning of a New Calmodulin–like Protein from Human Epidermis", The Journal of Biological Chemistry, vol. 275, No. 17, Apr. 28, 2000. Pp. 12841–12847.

COMPLETE™, Protease Inhibitor Cocktail Tablets, Roche Diagnostic GmbH, Penzberg, Germany.

MULTIPHOR™, Protein Electrophoresis Technical Manual, Amersham Biosciences, Freiburg, Germany.

* cited by examiner

Primary Examiner—Robert A. Wax
(74) Attorney, Agent, or Firm—Burns, Doane, Swecker & Mathis, L.L.P.

(57) ABSTRACT

The invention concerns an isolated polypeptide, of the family of calcium-fixing proteins, a mixture of polypeptides derived from proteolysis of the isolated polypeptide, compositions containing them, the uses of said polypeptide and a cosmetic treatment method for dry skin, hyperkeratosis, parakeratosis, psoriasis, ichthyosis, neoplasia. The invention also concerns a deoxyribonucleic acid sequence coding for said polypeptide and the uses of said deoxyribonucleic sequence.

21 Claims, No Drawings

ISOLATED PEPTIDE OF THE HORNY LAYER AND USER THEREOF

The invention has as its object an isolated polypeptide from the family of the calcium-fixing proteins, a mixture of polypeptides obtained from the proteolysis of the isolated polypeptide, compositions that contain them, the uses of said polypeptide and a cosmetic treatment process that is intended to treat dry skin, hyperkeratosis, parakeratosis, psoriasis, ichthyosis, and neoplasias. The invention also has as its object a deoxyribonucleic acid sequence that codes for said polypeptide and the uses of said deoxyribonucleic acid sequence.

The key role of the calcium flows in the cellular functions has been extensively described for more than 20 years. The calcium is thus an intracellular messenger of outstanding importance. Numerous hormones and extracellular messengers exert their effect by an increase of the intracellular ratio of calcium. It was quickly shown that most of the effects of the calcium were determined by a large, relatively homogeneous family of calcium-binding proteins. Among this family, the calmodulins are the most ubiquitous. The role of the calmodulin is to recognize the changes in the concentration of cytosolic calcium ions and to transmit the information to the intracellular proteins.

The transmission of the signal is carried out when the calmodulin binds the calcium during an increase of the cell ratio of the latter. This brings about changes in conformation of the protein which increases considerably its affinity for the target protein.

In terms of configuration, the free calcium calmodulin contains two globular domains that are connected by a flexible arm. Each domain contains two well-defined "helix-loop-helix" patterns that are known under the name of "EF-Hands" and that are responsible for the bond with calcium. The bond with the calcium induces a very significant conformational change. This conformational change is reflected by a presentation of the globular hydrophobic portion of the protein that allows the calmodulin to recognize and to bind to certain proteins with a high affinity. The bond of the calmodulin with its target protein then leads to the creation of an active complex.

The calmodulin is known for interacting with numerous proteins or enzymes as well as with numerous hydrophobic pharmaceutical agents or else with peptides of natural origin or synthetic origin.

In this regard, it is possible to cite

Certain protein-kinases involved in the cellular homeostasis and in certain critical cellular functions such as metabolism, motility, the transcription of genes and the cellular division, the proliferation;

The calcineurin that is a phosphatase that has a role in the regulation of enzymes and proteins that are involved in the transduction of the calcium signal;

The phosphodiesterase with cyclic nucleotides, the guanidylcyclase and the adenylylcyclase thus regulating in a positive manner and/or in a negative manner the ratios of the AMP-cyclic and GMP-cyclic second messengers in the mechanism of action of certain hormones;

The three isoforms of the NO-synthase that occur in the production of NO and thus in the vascular relaxation, the cytotoxic action of the macrophages, the release of neurotransmitters, neuropeptides and/or hormones;

Certain vital cytoskeleton proteins in the monitoring of the shape of cells, their rigidity and their adhesion, such as, for example, myosin;

Caldesmon, spectrins, adducin, proteins that bind to actin;

Desmocalmin, a protein of the desmosome that interacts with the keratins;

The plasma-membrane $Ca^{2+}$-ATPases that occur in the maintenance of the intracellular ion concentration;

Ornithine decarboxylase, certain A2 phospholipases and certain transglutaminases have been cited as being calmodulin-dependent.

In contrast, certain studies suggest that calmodulin has a role in the phenomena for reparation of deoxyribonucleic acid and that it potentially would be involved in aging of the skin.

It is known, finally, that if calmodulin is a well-described protein, it is actually the prototype of a large family of protein of which all of the individuals have not yet been described.

Thus, after long and laborious works, the applicant demonstrated, among the proteins of the epidermis, isolated and purified by biochemical techniques, a polypeptide that is expressed in the corneal epithelia. This polypeptide, otherwise called "CLSP" in the text (for skin protein similar to calmodulin: calmodulin-like skin protein) is expressed in the epidermis. It is known that in the corneal epithelia, the very large majority of expressed proteins is constituted by keratins. Thus, it is only by working out a particular extraction method that eliminates the keratins that the applicant was able to isolate and then to purify the CLSP.

The applicant then determined the primary amino acid sequence.

The invention therefore has as its object an isolated and purified polypeptide that belongs to the family of the calcium-fixing proteins (CaBP: calcium binding protein), characterized by the fact that it corresponds to the amino acid sequence SEQ ID NO: 1 below:

| Met | Ala | Gly | Glu | Leu | Thr | Pro | Glu | Glu | Glu | 10 |
|---|---|---|---|---|---|---|---|---|---|---|
| Ala | Gln | Tyr | Lys | Lys | Ala | Phe | Ser | Ala | Val | 20 |
| Asp | Thr | Asp | Gly | Asn | Gly | Thr | Ile | Asn | Ala | 30 |
| Gln | Glu | Leu | Gly | Ala | Ala | Leu | Lys | Ala | Thr | 40 |
| Gly | Lys | Asn | Leu | Ser | Glu | Ala | Gln | Leu | Arg | 50 |
| Lys | Leu | Ile | Ser | Glu | Val | Asp | Ser | Asp | Gly | 60 |
| Asp | Gly | Glu | Ile | Ser | Phe | Gln | Glu | Phe | Leu | 70 |
| Thr | Ala | Ala | Arg | Lys | Ala | Arg | Ala | Gly | Leu | 80 |
| Glu | Asp | Leu | Gln | Val | Ala | Phe | Arg | Ala | Phe | 90 |
| Asp | Gln | Asp | Gly | Asp | Gly | His | Ile | Thr | Val | 100 |
| Asp | Glu | Leu | Arg | Arg | Ala | Met | Ala | Gly | Leu | 110 |
| Gly | Gln | Pro | Leu | Pro | Gln | Glu | Glu | Leu | Asp | 120 |
| Ala | Met | Ile | Arg | Glu | Ala | Asp | Val | Asp | Gln | 130 |
| Asp | Gly | Arg | Val | Asn | Tyr | Glu | Glu | Phe | Ala | 140 |
| Arg | Met | Leu | Ala | Gln | Glu | | | | | 146 |

The polypeptide of the invention can be of natural or synthetic origin. Synthetic is defined here as any polypeptide that is obtained chemically or by production in an organism after introduction into this organism of elements that are necessary for this production.

The polypeptide of the invention can be obtained from any possible origin, namely either animal, in particular mammals and even more particularly human, or vegetable, either microorganisms (virus, phages, bacteria, i.a.) or else mushrooms, without prejudging whether or not they are present in a natural manner in said organism of origin.

Preferably, the polypeptide of the invention is of natural origin, purified from mammal tissues, particularly from mammal skin.

Preferably, the polypeptide of the invention is purified from human skin and even more preferably from human epidermis.

It is known that in a polypeptide, one or more amino acid residues can change for amino acid residues that have a similar hydropathic index without thereby changing the biological properties of the polypeptide. The hydropathic index is an index that is attributed to amino acids based on their hydrophobicity and their charge (Kyte et al. (1982), J. Mol. Biol, 157: 105).

The invention thus also has as its object a polypeptide as described above in which at least one amino acid residue has been changed for an amino acid residue that has a similar hydropathic index.

It is known that in general, the mature polypeptides that are found in the cells are obtained from the maturation of precursors that contain in their sequence the sequence of the mature polypeptide.

The invention thus also relates to any polypeptide, natural or synthetic, whose sequence partly consists of the sequence of the polypeptide of the invention.

It is known that the polypeptides can undergo post-translational modifications such as the formation of disulfide bonds, specific proteolytic cleavages, the addition of glucides (glycosylation), phosphorylation in particular at the level of serines and/or threonines and/or tyrosines, and/or the combination with lipids.

The polypeptide of the invention may have undergone one or more post-translational modifications.

The invention thus also relates to the polypeptide of the invention that may or may not have undergone post-translational modifications.

It is known to classify the polypeptides based on their isoelectric point.

The theoretical isoelectric point of the polypeptide of the invention can be derived from its amino acid scheme. The polypeptide of the invention is a theoretically acidic polypeptide.

The invention thus has as its object a polypeptide whose theoretical isoelectric point is between 1 and 6, particularly between 3 and 5. The polypeptide of the invention has a theoretical isoelectric point of 4.075.

It is known that the primary amino acid sequence as well as the various post-translational modifications undergone by a polypeptide ensure that said polypeptide can be characterized by its apparent molecular weight that is expressed in kilodaltons.

Apparent molecular weight is defined as the molecular weight that is obtained for the polypeptide by comparison of the electrophoretic mobility of the latter with those of standard proteins of molecular weight that are known on polyacrylamide/sodium dodecylsulfate gel, or else by comparison of the elution volume of the polypeptide with that of standard proteins of molecular weight known by exclusion chromatography (according to the techniques described in "Protein Purification," J.-C. Janson and L. Ryden, VCH Publisher Inc., N.Y., 1989).

The knowledge of the amino acidscheme of the polypeptide of the invention makes it possible to determine the theoretical molecular weight.

The invention therefore relates to a polypeptide that has a theoretical molecular weight of between 13 and 17-kilodaltons (kD), particularly between 14 and 16 kilodaltons (kD).

Very particularly, the polypeptide of the invention has a theoretical molecular weight of 15.9 kilodaltons (kD).

It further known that the primary amino-acid sequence of a polypeptide determines sites that are specifically recognized by proteases that, once the recognition of these sites is completed, will, with or without fixing to said polypeptide, induce its cleavage by proteolysis.

The invention thus also relates to at least one mixture of polypeptides obtained from the proteolysis of the invention.

It is therefore understood that in the text and unless otherwise stated, polypeptide is defined as the natural or synthetic polypeptide of the invention as described above or at least one of its fragments, whether it be obtained by proteolysis or in a synthetic manner or else any natural or synthetic polypeptide whose sequence consists totally or partially of the polypeptide sequence described above.

The analysis of the primary amino acid sequence of the polypeptide of the invention shows that the latter contains particular sites that are recognized as participating, in calcium-fixing polypeptides, in the development of the calcium-fixing site or sites. The calcium-fixing by the polypeptide of the invention is furthermore confirmed by the results of tests further presented in the examples.

The polypeptide of the invention is a calcium-fixing polypeptide.

Furthermore, the importance of the presence in the organism of the proteins of the calmodulin family is seen in the text. The importance of being able to provide to the organism a protein of the calmodulin family so as to modify the effects of the latter then is understood. The potential applications therefore cover all the pathways for the transduction of the calcio-dependent signal.

For example, in cosmetics, the protein of the invention can be used to regulate the impairments of epidermal, normal or pathological proliferation or differentiation (dry skin, hyperkeratosis, parakeratosis, psoriasis, ichthyosis, neoplasia . . . ), in the treatment of aging, particularly aging of the skin, and in the treatment of skin damage linked to exposure to ultraviolet radiation.

Thus, another object of the invention is therefore to provide compositions that comprise, in a physiologically acceptable medium, at least one polypeptide as described above.

According to the invention, a physiologically acceptable medium is a cosmetically and/or pharmaceutically acceptable medium that is compatible with the skin, the mucous membranes, the nails and the hair.

The compositions of the invention can be cosmetic or pharmaceutical compositions.

The compositions of the invention are preferably applied to the skin or the mucous membranes.

The polypeptide of the invention can be used as an agent that regulates the impairments of epidermal, normal or pathological proliferation or differentiation particularly in the treatment of dry skin, hyperkeratosis, parakeratosis, psoriasis, ichthyoses, and neoplasias. The polypeptide of the invention thus can be introduced into a composition that is intended for the moisturizing and/or making up of the skin, mucous membranes and/or keratinic fibers.

The composition of the invention is also intended to fight against the signs of aging of the skin and/or to fight against the effects of ultraviolet radiation, particularly of A or B type.

Another object of the invention is therefore a composition that is intended to treat the impairments of epidermal proliferation or differentiation, dry skin, hyperkeratosis, parakeratosis, psoriasis, ichthyoses, and/or neoplasias.

It also relates to a composition that comprises at least one polypeptide of the invention for fighting against the signs of aging of the skin and/or for fighting against the effects of ultraviolet radiation, particularly of A or B type.

Another object of the invention relates to the use of at least one polypeptide of the invention in a composition or for the preparation of a composition, whereby the polypeptide or the composition is intended to treat the impairments of epidermal proliferation or differentiation, dry skin, hyperkeratosis, parakeratosis, psoriasis, ichthyoses, and/or neoplasias.

It also relates to the use of at least one polypeptide of the invention as an agent for treating the signs of aging of the skin and/or for fighting against the effects of ultraviolet radiation, particularly of A or B type.

Another object of the invention is also a process for cosmetic treatment that is intended to fight against the cutaneous signs of impairments of epidermal proliferation and/or differentiation such as dry skin, hyperkeratosis, parakeratosis, psoriasis, ichthyoses, and/or neoplasias, the signs of aging of the skin and/or the effects of ultraviolet radiation, particularly of A or B type, characterized by the fact that a cosmetic composition that comprises at least one polypeptide of the invention is applied to the skin, the mucous membranes and/or the keratinic fibers.

The process for treatment of the invention is a cosmetic process that is intended to improve the aesthetic appearance of the individual who is experiencing difficulties in epidermal proliferation and/or differentiation.

The amount of polypeptide that is contained in the composition of the invention is, of course, based on the desired result and can therefore vary to a wide extent.

To provide an order of magnitude, the composition can contain the polypeptide of the invention in an amount that represents 0.00001% to 50% of the total weight of the composition and preferably in an amount that represents 0.001% to 10% of the total weight of the composition and even more preferably in an amount that represents 0.1% to 1% of the total weight of the composition.

The invention also has as its object the use of the polypeptide of the invention or its proteolysis fragments and any synthetic peptide that is derived from its sequence, to prepare or to purify, optionally from the epidermis, any structural or functional molecule that can be bound specifically to said isolated polypeptide or to said isolated proteolysis fragments or to said synthetic peptide.

In this regard, the applicant demonstrated that the polypeptide of the invention can, for example, be bound to at least one protein target that is selected from among the transglutaminases, particularly transglutaminase 3, galectin 7, the annexins, particularly annexins 2, MRP14 or calgranulin B, the heparanases, HSP 27, SCCE or else the riobosomal protein L9 of 60S.

To the extent that it is known that the transglutaminases play a significant role in the formation of corneal casings, it is possible to assume that the CLSP plays a regulating role in the formation of corneal casings through the fixing to the transglutaminase.

The invention thus has as its object the use of the polypeptide of the invention or its proteolysis fragments and any synthetic peptide derived from its sequence for regulating the transglutaminases, particularly transglutaminase 3 and thus for regulating the formation of the corneal layer of the epidermis.

To the extent that the polypeptide of the invention belongs to the family of calmodulins and that it is known that the polypeptides of this family are in general second-messengers that respond to a stimulus (the intracellular calcium ratio) via a fixing to their target protein, it is possible to use the polypeptide of the invention to prepare or to purify, optionally from the epidermis, any structural or functional molecule that can modulate the interaction between the polypeptide of the invention and its possible ligands.

The invention thus has as its object the use of the polypeptide of the invention or it's proteolysis fragments and any synthetic peptide that is derived from its sequence to prepare or to purify, optionally from the epidermis, any structural or functional molecule that can modulate the interaction between the polypeptide of the invention and its possible ligands.

The invention also has as its object the use of the polypeptide of the invention or its proteolysis fragments or any synthetic peptide that is derived from its sequence to prepare antiserums and/or specific monoclonal antibodies whose purpose in particular is to purify this protein and its fragments. By extension, the invention also has as its object any use of said sequence to produce antibodies or recombinant antibody fragments, regardless of the biological system that is used to produce the latter.

The invention also has as its object a polyclonal or monoclonal antibody that is characterized by the fact that it specifically recognizes the polypeptide of the invention.

The antibody may be an antibody that is prepared by immunization of any animal type that can be used for this purpose, particularly the rabbit. The antibody may be prepared by immunization with the polypeptide of the invention whether the latter is of natural or synthetic origin, purified or not.

It is known that a protein is synthesized in the cells from a deoxyribonucleic acid matrix that codes for said protein. It is also known that the genetic code is degenerated. Thus, the amino acid sequence of the polypeptide of the invention can be obtained from different deoxyribonucleic acid sequences, natural or synthetic. Synthetic deoxyribonucleic acid sequence is defined here as any sequence that is obtained chemically or by genetic manipulation.

Said deoxyribonucleic acid sequences can be obtained from any possible origins, namely either animal, in particular mammals and still more particularly human, or vegetable, either microorganisms (virus, phages, bacteria, i.a.) or else mushrooms, without prejudging whether or not they are present in a natural manner in said organism of origin.

The applicant isolated, purified and sequenced a fragment of deoxyribonucleic acids coding for the polypeptide of the invention by molecular biology techniques, in particular the screening of complementary deoxyribonucleic acid expression banks prepared from human epidermis.

The invention therefore has as its object a cosmetic or pharmaceutical composition that comprises, in a physiologically acceptable medium, all deoxyribonucleic acid sequences, natural or synthetic, of which all or part codes for the primary amino acid sequence of the polypeptide of the invention.

During these works, the applicant was able to isolate and to purify a deoxyribonucleic acid sequence that codes for the primary amino acid sequence of the polypeptide of the invention from human skin.

The invention has as its object a deoxyribonucleic acid fragment that is isolated and purified corresponding to the nucleotide sequence that codes SEQ ID NO: 2 below:

```
AATTCCCGGA TCCCTGCGGC TGCCTGCACT CTGGACCACG    40

AGCTCTGAGA GCAGCAGGTT GAGGGCCGGT GGGCAGCAGC    80

TCGGAGGCTC CGCGAGGTGC AGGAGACGCA GGCATGGCCG   120

GTGAGCTGAC TCCTGAGGAG GAGGCCCAGT ACAAAAAGGC   160

TTTCTCCGCG GTTGACACGG ATGGAAACGG CACCATCAAT   200

GCCCAGGAGC TGGGCGCGGC GCTGAAGGCC ACGGGCAAGA   240

ACCTCTCGGA GGCCCAGCTA AGGAAACTCA TCTCCGAGGT   280

TGACAGCGAC GGCGACGGCG AAATCAGCTT CCAGGAGTTC   320

CTGACGGCGG CAAGGAAGGC CAGGGCCGGC CTGGAGGACC   360

TGCAGGTCGC CTTCCGCGCC TTCGACCAGG ATGGCGACGG   400

CCACATCACC GTGGACGAGC TCAGGCGGGC CATGGCGGGG   440

CTGGGGCAGC CGCTGCCGCA GGAGGAGCTG GACGCCATGA   480

TCCGCGAGGC CGACGTGGAC CAGGACGGGC GGGTGAACTA   520

CGAGGAGTTC GCGAGGATGC TCGCCCAGGA GTGAGGCTCC   560

CCGCCTGTGT CCCCCTGGCT GCGCTCTGAG CCTTCAGGGC   600

CACCGCCCGC TGCTGCTTTT GTGCTGGGAC TCTCCGGGGA   640

AACCTGGTCG GTGGATGGGA AACTGCCTCC CCCTGGGAGG   680

AAGGCTTTGC GCTCCGGGGC CTGGATGCGG CGCCCTCGGG   720

CCGCCTGCGA GCCCCTCTCT GCCTTCAGAC CTTGGGCAGA   760

AGGAGGCCTC CTTGGGCCTG GTCCCCCTTT GCCCTGCAGT   800

GGAATGAGGG CCCCTTAACC CCGCATTGAT CTAAATAAAG   840

GACTGCCGAG TTCCAAAA                          858
```

The invention also has as its object any isolated and purified deoxyribonucleic acid fragment that comprises at least the nucleotide sequence that codes SEQ ID NO: 2.

The invention also has as its object any polynucleotide, ribonucleic acid or deoxyribonucleic acid, sense or antisense, that corresponds at least to the nucleotide sequence that codes SEQ ID NO: 2.

The DNA fragment that corresponds to the sequence SEQ ID NO: 2 can be introduced into an expression vector that thus makes possible the synthesis of a so-called recombinant protein that corresponds to the CLSP.

Recombinant protein is defined here as any peptide element that corresponds to all or part of the peptide sequence of the CLSP, obtained artificially after introduction and expression of all or part of the complementary DNA of the CLSP in any expression vector, regardless of the organism that allows this expression.

Particularly according to the invention, the CLSP or a portion of the CLSP can be produced after introduction of all or part of the nucleotide sequence that codes SEQ ID NO: 2 in an expression vector such as, for example, the vector pGex-2T (Amersham Pharmacia Biotech Inc.) and expression in E. coli.

The invention therefore also has as its object a recombinant expression vector that contains all or part of the nucleotide sequence that codes SEQ ID NO: 2.

The invention also has as its object a recombinant protein that corresponds to all or part of the sequence SEQ ID NO: 1, particularly the one that is obtained by expression of an expression vector pGex-2T that contains all or part of the sequence that codes SEQ ID NO: 2.

The invention also has as its object a cosmetic or pharmaceutical composition that comprises, in a physiologically acceptable medium, at least one isolated and purified deoxyribonucleic acid fragment that comprises at least one nucleotide sequence that codes SEQ ID NO: 2.

The invention also has as its object a cosmetic or pharmaceutical composition that comprises, in a physiologically acceptable medium, a sequence of sense or antisense ribonucleic acids that correspond to said sequence SEQ ID NO: 2.

It also has as its object the use of said deoxyribonucleic acid sequences for the production of the polypeptide of the invention or a ribonucleic acid that corresponds by any known technique such as, for example, in vitro synthesis, from reconstituted media or synthesis by organisms or microorganisms.

Regardless of their nature, the compositions of the invention can be ingested, injected or applied on the skin (on any cutaneous zone of the body) or the mucous membranes (oral, jugal, gingival, genital, conjunctival, . . . ).

According to the method of administration, the compositions according to the invention can come in all the galenical forms that are normally used.

For a topical application on the skin, the composition can have the form in particular of aqueous solution or oily solution or lotion-type dispersion or serum, cream-type emulsions of liquid or semi-liquid consistency, obtained by dispersion of a fatty phase into an aqueous phase (H/E) or vice versa (E/H), or suspensions or emulsions of soft consistency of cream type or aqueous gel type or anhydrous type, or else microcapsules or microparticles, or vesicular dispersions of ionic type and/or non-ionic type or foams or else in the form of compositions for aerosol that also comprise a pressurized propellant. These compositions are prepared according to common methods.

For the injection, the composition can come in the form of aqueous lotion, oily lotion or in the form of serum. For the eyes, it can come in the form of drops, and for ingestion, it can come in the form of capsules, granules, syrups or tablets.

The amounts of different components of the compositions according to the invention are those conventionally used in the areas under consideration.

These compositions constitute in particular creams for cleaning, screening, treatment or moisturizing for the face, for the hands, for the feet, for the large anatomical folds or for the body (for example, day creams) night creams, make-up removal creams, make-up foundation creams, sun-block creams), liquid make-up removers, cleansing creams, screening or moisturizing body lotions, sun-block creams, after-sun creams, lotions, gels or foams for moisturizing skin, such as cleansing lotions, sun-block lotions, after-sun lotions, artificial tanning lotions, compositions for the bath, deodorizing compositions that comprise a bactericidal agent, aftershave gels or lotions, depilatory creams, insect repellents, pain-relief compositions, compositions to treat certain skin diseases such as eczema, rosacea, psoriasis, lichens, severe pruritis, and ichthyosis.

The compositions according to the invention can also consist of solid preparations that consist of soaps or cleansing bars.

The compositions can also be packaged in aerosol form, to include a pressurized propellant.

The composition according to the invention can also be a composition for care of the scalp, in particular a shampoo, a curling lotion, a medicating lotion, a styling cream or gel, a compound of dyes (in particular oxidation dyes) optionally in the form of coloring shampoos, hair restructuring lotions, a permanent compound (in particular a compound for a first permanent), a hair-loss prevention lotion or gel, a lice-control shampoo, anti-dandruff compositions, etc.

The composition can also have an oral-dental use, for example a toothpaste. In this case, the composition can contain common-adjuvants and additives for the compositions for oral use and in particular surfactants, thickening agents, moisturizers, polishing agents such as silica, various active ingredients such as fluorides, in particular sodium fluoride, and optionally sweeteners such as sodium saccharinate.

When the composition is an emulsion, the proportion of the fatty phase can go from 5% to 80% by weight and preferably 5% to 50% by weight relative to the total weight of the composition. The oils, the waxes, the emulsifiers and the co-emulsifiers that are used in the composition in emulsion form are selected from among those that are conventionally used in the cosmetic domain. The emulsifier and the co-emulsifier are present in the composition in a ratio of from 0.3% to 30t by weight and preferably from 0.5 to 20% by weight relative to the total weight of the composition. The emulsion can also contain lipid vesicles.

When the composition is an oily solution or an oily gel, the fatty phase can represent more than 90% of the total weight of the composition.

In a known way, the cosmetic composition can also contain usual adjuvants in the cosmetic domain, such as the hydrophilic or lipophilic solidifiers, the hydrophilic or lipophilic additives, the preservatives, the antioxidants, the solvents, the perfumes, the feedstocks, the filters, the odor absorbers and the coloring materials. The amounts of these different adjuvants are those conventionally used in the cosmetic domain, and, for example, from 0.01% to 10% of the total weight of the composition. These adjuvants, according to their nature, can be introduced in the fatty phase, in the aqueous phase and/or in the lipid spheres.

As oils or waxes that can be used in the invention, it is possible to cite the mineral oils (vaseline oil), vegetable oils (liquid fraction of karite butter, sunflower seed oil), animal oils (perhydrosqualene), synthesis oils (purcellin oil), siliconized oils or waxes (cyclomethicone) and fluorinated oils (perfluoropolyethers), beeswax, carnauba wax or paraffin wax. It is possible to add to these oils fatty alcohols and fatty acids (stearic acid).

As emulsifiers that can be used in the invention, it is possible to cite, for example, glycerol stearate, polysorbate 60 and the PEG-6/PEG-32/glycol stearate mixture that is sold under the name of Tefose$^R$ 63 by the Gattefosse Company.

As solvents that can be used in the invention, it is possible to cite the lower alcohols, in particular ethanol and isopropanol, and propylene glycol.

As hydrophilic solidifiers that can be used in the invention, it is possible to cite the carboxyvinyl polymers (carbomer), acrylic copolymers such as the copolymers of acrylates/alkylacrylates, the polyacrylamides, the polysaccharides such as hydroxypropylcellulose, the natural gums and the clays, and, as lipophilic solidifiers, it is possible to cite modified clays such as bentones, inorganic salts of fatty acids such as the aluminum stearates and hydrophobic silica, ethyl cellulose, and polyethylene.

The composition can contain other hydrophilic active substances such as the proteins or protein hydrolysates, amino acids, polyols, urea, allantoin, sugars and sugar derivatives, water-soluble vitamins, vegetable extracts and hydroxy acids.

As lipophilic active substances, it is possible to use retinol (vitamin A) and its derivatives, tocopherol (vitamin E) and its derivatives, essential fatty acids, ceramides, essential oils, and salicylic acid and its derivatives.

According to the invention, the composition can combine at least one extract of at least one iridace with other active agents that are intended in particular for prevention and/or treatment of skin ailments. Among these active agents, it is possible to cite by way of example:

The agents that reduce the differentiation and/or the proliferation and/or the skin pigmentation such as retinoic acid and its isomers, retinol and its esters, vitamin D and its derivatives, estrogens such as estradiol, kojic acid or hydroquinone;

The antibacterial agents such as clindamycin phosphate, erythromycin or the tetracycline-class antibiotics;

The lice-control agents, in particular metronidazole, crotamiton or the pyrethrinoids;

The anti-fungals, in particular the compositions that belong to the imidazole class such as econazole, ketoconazole or miconazole or their salts, the polyene compositions, such as amphotericin B, the compositions of the allylamine family, such as terbinafine or else octopirox;

Antiviral agents such as acylclovir;

steroidian anti-inflammatory agents, such as hydrocortisone, betamethasone valerate or clobetasol propionate, or non-steroidian anti-inflammatory agents, such as, for example, ibuprofen and its salts, diclofenac and its salts, acetylsalicylic acid, acetaminophen or glycyrrhizic acid;

Anesthetic agents such as lidocaine chlorohydrate and its derivatives;

Antipruritic agents such as thenaldine, trimeprazine, or cyproheptadine;

Keratolytic agents such as the α- and β-hydroxycarboxylic acids or β-ketocarboxylic acids, their salts, amides or esters and more particularly the hydroxy acids such as glycolic acid, lactic acid, salicylic acid, citric acid and, in general, the acids of fruits and n-octanoyl-5-salicylic acid;

The hydrating agents such as glycerol and its derivatives;

The free anti-radical agents, such as α-tocopherol or its esters, the superoxide dismutases, certain metal chelating agents or ascorbic acid and its esters;

The anti-seborrhea agents such as progesterone;

The anti-dandruff agents such as octopirox or zinc pyrithione

The anti-acne agents such as retinoic acid or benzoyl peroxide;

The extracts of vegetable origin or bacterial origin.

Thus, according to a particular embodiment, the composition according to the invention also comprises at least one agent that is selected from among the antibacterial agents, lice-control agents, anti-fungal agents, antiviral agents, anti-inflammatory agents, antipruritic agents, anesthetic agents, keratolytic agents, free anti-radical agents, anti-seborrhea agents, anti-dandruff agents, anti-acne agents and/or the agents that reduce the differentiation and/or the proliferation and/or the skin pigmentation.

EXAMPLE 1

Materials and Methods

The cDNA keratinocyte library cloned in λgt11 (origin of mRNA=keratinocytes of adult human foreskins) is obtained from Clontech (Palto Alto, Calif., USA).

The oligomers that are used in the different experiments are presented below:

| Name of the oligomer | Derived from | Position | Sequence 5' to 3' |
|---|---|---|---|
| sc5 (sense) | CLSP | 168/191 | GC (N) GT (N) GA (Y) AC (N) GA (Y) GG (N) AA (Y) GG (N) (SEQ ID NO. 3) |
| sc10 (antisense) | CLSP | 535/554 | TCACTCCTGGGCGACGATC (SEQ ID NO. 4) |
| sc16 (antisense) | CLSP (+RS) | 533/555 | TTGAATTCTCACTCCTGGGCGAGC ATCCTC (SEQ ID NO. 5) |
| sc21 | CLSP | 240/257 | CTGGGCCTCCAGAGGTT (SEQ ID NO. 6) |
| sc29 | CLSP (+RS) | 113/140 | GATAGGATCCATGGCCGGTGAGCT GACTCCTGAGGAG (SEQ ID NO. 7) | sc7 is the SK-primer oligomer sold by the Stratagene Company, Not I-(dT)$_{18}$ is a primer sold by the Amersham Pharmacia Biotech Company N = A, C, G or T
Y = C or T
(+RS): Restriction site(s) added to the sequence in the oligomer Degenerated oligomer sc5 is based on the amino acid sequence SEQ ID NO: 1. All of the other oligomers derived from CLSP and their position are derived from nucleotide sequence SEQ ID NO: 2.

Not I-(dT)$_{18}$ is designed for attaching to long series of A, for example the polyA+. Used in the reverse transcription reactions, Not I-(dT)$_{18}$ attaches to polyA+.

1. Preparations from the Human Stratum Corneum Buffers:

I:SDS 0.3%; tris-HCl 28 mmol; tris-base 22 mmol

2D:8 M urea; 2% CRAPS (3-(3-cholamidopropyl)-dimethylamonio-1-propane-sulfonate); dithiothreitol 20 mmol; 0.5% imobilin pH gradient buffer (Amersham Pharmacid Tiotech), pH=3;

For the purification of the CLSP, acetone extracts of the stratum corneum were prepared according to the method described by Lundstrom and Egelrüd in Acta Derm. Venerol., 1991, 71: 471–474.

78 mg of acetone powder was thus prepared.

2.5 ml of buffer I is added to 78 mg of acetone powder, and the whole is potterized, brought to boiling for 10 minutes and then repotterized. The solution is then centrifuged at 10,000 g for 10 minutes. The supernatant is collected and filtered with 0.22 M. 2 ml of supernatant S1 thus is obtained.

10 ml of cold acetone (10V/2V) is then added to supernatant S1. It is left in the cold (stacked ice) for 10 minutes, and it is centrifuged at 9400 g for 20 minutes at 4° C.

The supernatant is then eliminated, and the cap is dried at ambient temperature for 20 minutes. The cap is then taken up in 30 l of buffer 2D. Extract E1 is thus obtained.

2. Bidimensional Gel

The separation into two dimensions of the proteins that are contained in extract E1 is carried out in a Pharmacia-brand device MULTIPHOR™ model) according to the recommendations of the supplier.

The coloring of the spots, the recovery of the latter and the sequencing of the polypeptide that they contained were carried out according to standard techniques described in "Gel Electrophoresis of Proteins" (IRL Press) or else "A Practical Guide to Protein and Peptide Purification for Microsequencing" (Paul Matsudaira, Editor, Second Edition, 1993).

3. Cloning and Sequencing of cDNA CLSP:

The total RNA of keratinocytes of an epidermal equivalent (Episkin) were prepared with an RNeasy Kit preparation kit and purified with a QIA shredder column kit of the Qiagen brand according to the specifications of the supplier.

The additional DNA of the thus prepared RNA were synthesized with a First Strand cDNA Synthesis Kit of Amersham Pharmacia Biotech brand according to the specifications of the supplier by using the NotI-d(T)18 oligomer.

A cDNA with 775 pairs of bases that is thus obtained was amplified by polymerization chain reactions (PCR) in a thermal cycle device of Perkin-Elmer brand (Thermocycler model) by using a pfu polymerase of Stratagene brand and the scS/NotI-d(T)18 oligomer pair. A sequencing of this fragment made it possible to determine from it the nucleotide scheme.

To obtain the complete sequence of cDNA of the CLSP, PCR reactions were carried out with the following oligomer pairs sc10/sc7, sc7/sc21, sc16/sc29 under standard experiment conditions on a DNA bank complementary to keratinocytes cloned in phage gt11 (Stratagene).

The homology research was carried out via the WU-Blast program on the Internet site Expasy Swissprot; the detection of possible cleavage sites is carried out via the Omiga 1.1 PC program (Oxford Molecular, Oxford, U.K.).

Design and Expression of a Recombinant CLSP Protein:

The cDNA of the CLSP is introduced in the pGex-2T vector (Pharmacia Biotech Inc.) by cutting/binding to the BamH-1/EcORI restriction sites. The design for which the coding sequence of the CLSP is in phase with the sequence of the glutathione S-transferase contained in the vector is then introduced into the *E. coli* BL21 bacterium. The recombinant protein that is expressed by the bacteria can be cut by the thrombin, whereby the design is such that the fusion protein that is obtained carries a site for cutting by this protease. All of these experiments were carried out by strictly applying the various protocols of the suppliers.

Calcium-fixing by the CLSP:

The fusion protein that is obtained above is deposited on an SDS-PAGE-type gel in the presence or in the absence of ethylene diamine tetraacetate (EDTA), chelating agent of calcium ions, according to the protocol described by Burgess et col. (BBA, 623 (1980), 257–270).

Affinity Chromatography:

Affinity chromatography columns have been produced with 1 ml of ball.

The polypeptide of the invention was immobilized on sepharose balls activated with cyanogen bromide that is obtained from Amersham Pharmacia Biotech and according to the recommendations of the manufacturer by using 1.3 mg of polypeptide per milliliter of balls.

The coupling efficiency was 0.95 mg of polypeptide per milliliter of balls. Human epidermis (0.83 g of abdominal skin obtained from plastic surgery and 100 g of plantar stratum corneum) was homogenized with polytron in 10 ml and 120 ml respectively of 10 mmol of Herpes buffer, pH 7.4, containing 150 mmol of sodium chloride, 0.1% (weight/volume) of triton X100 and a mixture of protease inhibitors COMPLETE™ EDTA-free of Roche Molecular diluted with 1 M of depepstatin).

The suspension is then centrifuged at 10,000 g for 10 minutes at 4° C. The supernatant is filtered at 0.22 and adjusted with 2.5 mmol of calcium chloride before passing at ambient temperature through the affinity column. The columns are then washed with 10 volumes of 10 mmol Hepes buffer, pH 7.4, containing 150 mmol of sodium chloride, 0.1% (weight/volume) of triton X100 and a mixture of protease inhibitors. The elution is carried out by using the same buffer that contains 5 mmol of EDTA instead of 2 mmol of calcium chloride.

The eluted proteins are subjected to a denaturing gel electrophoresis (SDS-PAGE) and after migration, they are colored with silver with a silver coloration kit of the Amersham Pharmacia Biotech Company and according to the recommendations of the manufacturer.

Results

Purification and Characterization of the CLSP

Among all of the spots that are analyzed from the bidmensional gel, the sequence that is derived from one of the spots provided a sequence homology with the calmodulin that is important enough to be retained but different enough for its analysis to be pursued.

From the amino acid sequence elements that are obtained and by the molecular biology techniques described above, it was possible to isolate and to purify the sequence SEQ ID NO: 1.

The sequence homologies between this protein and the calmodulin allow one to think that this protein should have properties similar to those of calmodulin.

Four calcium-fixing sites can be demonstrated in this sequence, namely the sites between amino acids 21 and 32, 57 and 68, 91 and 102, and 127 and 138.

The electrophoretic migration experiments, particularly with the recombinant protein, carried out in the presence or in the absence of calcium ions confirm that the protein fixes the calcium.

This sequence therefore corresponds to a complete calcium-fixing protein that is not calmodulin and that is present in the stratum corneum of the human epidermis.

Cloning of the DNA of the SCTE:

By the techniques described above, a DNA with 858 pairs of bases was isolated. This DNA fragment comprises the integral coding sequence of the CLSP, from the ATG codon at-position 114 up to the stop codon at position 552.

Affinity Chromatography:

The sequencing of one of the proteins held in the affinity column carried out with the polypeptide of the invention showed that it is a transglutaminase and particularly transglutaminase 3.

Other experiments showed that galectin 7, the annexins, particularly annexins 2, MRP14 or calgranulin B, the heparanases, particularly heparanase II, Heat Shock P 27, the SCCE or else the ribosomal L9 protein of 60S are also bound to the polypeptide of the invention.

What is claimed is:

1. A purified natural or synthetic polypeptide comprising amino acid sequence SEQ ID NO: 1:

```
Met Ala Gly Glu Leu Thr Pro Glu Glu Glu         10

Ala Gln Tyr Lys Lys Ala Phe Ser Ala Val         20

Asp Thr Asp Gly Asn Gly Thr Iie Asn Ala         30

Gln Glu Leu Gly Ala Ala Leu Lys Ala Thr         40

Gly Lys Asn Leu Ser Glu Ala Gin Leu Arg         50

Lys Leu Ile Ser Glu Val Asp Ser Asp Gly         60

Asp Gly Glu Ile Ser Phe Gln Glu Phe Leu         70

Thr Ala Ala Arg Lys Ala Arg Ala Gly Leu         80

Glu Asp Leu Gln Val Ala Phe Arg Ala Phe         90

Asp Gln Asp Gly Asp Gly His Ile Thr Val        100

Asp Glu Leu Arg Arg Ala Met Ala Gly Leu        110

Gly Gln Pro Leu Pro Gln Glu Glu Leu Asp        120

Ala Met Ile Arg Glu Ala Asp Val Asp Gin        130

Asp Gly Arg Val Asn Tyr Glu Glu Phe Ala        140

Arg Met Leu Ala Gin Glu                        146.
```

2. The polypeptide according to claim 1, wherein it is purified from animals.

3. The polypeptide according to claim 1, wherein it is purified from the skin of mammals.

4. The polypeptide according to claim 1, wherein it is purified from cultured or non-cultured human skin.

5. The polypeptide according to claim 1, wherein it is purified from the human epidermis.

6. A synthetic polypeptide whose sequence consists of the sequence of polypeptide as described in claim 1.

7. The polypeptide according to claim 1, wherein it has a theoretical isoelectric point between 1 and 6.

8. The polypeptide according to claim 1, wherein it has a theoretical molecular weight of between 13 and 17 kilodaltons (kD).

9. A mixture of polypeptides obtained from the proteolysis of polypeptide as described in claim 1.

10. The polypeptide according to claim 1, wherein a primary sequence of the polypeptide has at least one calcium-fixing site.

11. The polypeptide according to claim 1, wherein it fixes calcium.

12. A composition comprising in a physiologically acceptable medium an amount effective to regulate the impairments of normal or pathological epidermal proliferation or differentiation of at least one polypeptide as defined in claim 1.

13. A composition intended to regulate the impairments of normal or pathological epidermal proliferation or differentiation comprising, in a cosmetically acceptable medium, an effective amount of at least one polypeptide as defined in claim 1.

14. A composition for treating dry skin, hyperkeratosis, parakeratosis, psoriasis, ichthyoses, or neoplasias, comprising in a physiologically acceptable medium, an effective amount of at least one polypeptide as defined in claim 1.

15. The composition according to claim 12, which is intended for cosmetic or pharmaceutical application.

16. A method for the treatment of dry skin, hyperkeratosis, parakeratosis, psoriasis, ichthyoses, or neoplasias, comprising administering an effective amount of at least one polypeptide according to claim 1 to a patient in need of such treatment.

17. A method for regulating transglutaminases comprising administering an effective amount of at least one polypeptide according to claim 1 to a patient in need of such regulation.

18. The method according to claim 17, wherein the polypeptide or the composition is intended to regulate transglutaminase 3.

19. The composition according to claim 12, wherein the polypeptide or the composition is intended to regulate the formation of the corneal layer of the epidermis.

20. A method for treating dry skin, hyperkeratosis, parakeratosis, psoriasis, ichthyoses, neoplasias, wherein a cosmetic composition as described in claim 12 is applied on the skin of the subject to be treated.

21. Recombinant protein that is obtained by expression of an expression vector pGex-2T that contains all or part of a sequence that codes SEQ ID No. 1.

* * * * *

SEQUENCE LISTING

```
<160> NUMBER OF SEQ ID NOS: 7

<210> SEQ ID NO 1
<211> LENGTH: 146
<212> TYPE: PRT
<213> ORGANISM: Homo sapiens

<400> SEQUENCE: 1

Met Ala Gly Glu Leu Thr Pro Glu Glu Ala Gln Tyr Lys Lys Ala
 1               5                  10                  15

Phe Ser Ala Val Asp Thr Asp Gly Asn Gly Thr Ile Asn Ala Gln Glu
                20                  25                  30

Leu Gly Ala Ala Leu Lys Ala Thr Gly Lys Asn Leu Ser Glu Ala Gln
                35                  40                  45

Leu Arg Lys Leu Ile Ser Glu Val Asp Ser Asp Gly Asp Gly Glu Ile
        50                  55                  60

Ser Phe Gln Glu Phe Leu Thr Ala Ala Arg Lys Ala Arg Ala Gly Leu
65                  70                  75                  80

Glu Asp Leu Gln Val Ala Phe Arg Ala Phe Asp Gln Asp Gly Asp Gly
                85                  90                  95

His Ile Thr Val Asp Glu Leu Arg Arg Ala Met Ala Gly Leu Gly Gln
                100                 105                 110

Pro Leu Pro Gln Glu Glu Leu Asp Ala Met Ile Arg Glu Ala Asp Val
        115                 120                 125

Asp Gln Asp Gly Arg Val Asn Tyr Glu Glu Phe Ala Arg Met Leu Ala
        130                 135                 140

Gln Glu
145

<210> SEQ ID NO 2
<211> LENGTH: 858
<212> TYPE: DNA
<213> ORGANISM: Homo sapiens
```

<400> SEQUENCE: 2

```
aattcccgga tccctgcggc tgcctgcact ctggaccacg agctctgaga gcagcaggtt      60
gagggccggt gggcagcagc tcggaggctc cgcgaggtgc aggagacgca ggcatggccg     120
gtgagctgac tcctgaggag gaggcccagt acaaaaaggc tttctccgcg gttgacacgg     180
atggaaacgg caccatcaat gcccaggagc tgggcgcggc gctgaaggcc acggcaaga     240
acctctcgga ggcccagcta aggaaactca tctccgaggt tgacagcgac ggcgacggcg     300
aaatcagctt ccaggagttc ctgacggcgg caaggaaggc cagggccggc ctggaggacc     360
tgcaggtcgc cttccgcgcc ttcgaccagg atggcgacgg ccacatcacc gtggacgagc     420
tcaggcgggc catggcgggg ctggggcagc cgctgccgca ggaggagctg gacgccatga     480
tccgcgaggc cgacgtggac caggacgggc gggtgaacta cgaggagttc gcgaggatgc     540
tcgcccagga gtgaggctcc ccgcctgtgt cccctggct gcgctctgag ccttcagggc      600
caccgcccgc tgctgctttt gtgctgggac tctccgggga aacctggtcg gtggatggga     660
aactgcctcc ccctgggagg aaggctttgc gctccggggc ctggatgcgg cgccctcggg     720
ccgcctgcga gcccctctct gccttcagac cttgggcaga aggaggcctc cttgggcctg     780
gtccccttt gccctgcagt ggaatgaggg ccccttaacc ccgcattgat ctaaataaag      840
gactgccgag ttccaaaa                                                    858
```

<210> SEQ ID NO 3
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 3, 6, 12, 18, 24
<223> OTHER INFORMATION: n = A,T,C or G

<400> SEQUENCE: 3

```
gcngtngaya cngayggnaa yggn                                             24
```

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4

```
tcactcctgg gcgagcatc                                                   19
```

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5

```
ttgaattctc actcctgggc gagcatcctc                                       30
```

<210> SEQ ID NO 6
<211> LENGTH: 18
<212> TYPE: DNA
<213> ORGANISM: Artificial Sequence
<220> FEATURE:

-continued

```
<223> OTHER INFORMATION: primer

<400> SEQUENCE: 6
ctgggcctcc gagaggtt                                                18

<210> SEQ ID NO 7
<211> LENGTH: 37
<212> TYPE: DNA
<213> ORGANISM: Artificial Sequence
<220> FEATURE:
<223> OTHER INFORMATION: primer

<400> SEQUENCE: 7
gataggatcc atggccggtg agctgactcc tgaggag                           37
```